United States Patent [19]

Free

[11] Patent Number: 4,549,652
[45] Date of Patent: Oct. 29, 1985

[54] IUD PACKAGE

[75] Inventor: Michael J. Free, Seattle, Wash.

[73] Assignee: PIACT, Seattle, Wash.

[21] Appl. No.: 697,502

[22] Filed: Feb. 1, 1985

Related U.S. Application Data

[63] Continuation of Ser. No. 509,721, Jun. 29, 1983, abandoned.

[51] Int. Cl.⁴ .............................................. B65D 85/16
[52] U.S. Cl. .................................. 206/363; 128/130; 206/438
[58] Field of Search .................... 128/127, 130, 303 R; 206/306, 363, 364, 438, 439, 440, 441

[56] References Cited

U.S. PATENT DOCUMENTS

| | | | |
|---|---|---|---|
| 3,398,737 | 8/1968 | Sheppard et al. | 206/438 |
| 3,448,737 | 6/1969 | Huck | 206/438 |
| 3,612,038 | 10/1971 | Halligan | 206/364 |
| 3,752,309 | 8/1973 | Hopkins | 206/363 |
| 3,918,444 | 11/1975 | Hoff et al. | 128/130 |
| 3,918,445 | 11/1975 | Okamoto et al. | 128/130 |
| 3,965,891 | 6/1976 | Lerner | 128/130 |
| 3,967,728 | 7/1976 | Gordon et al. | 206/364 |
| 4,026,281 | 5/1977 | Mayberry et al. | 128/130 |
| 4,143,656 | 3/1979 | Holmes | 128/130 |
| 4,230,115 | 10/1980 | Walz, Jr. et al. | 206/364 |
| 4,428,371 | 1/1984 | Krzeminski | 128/127 |

Primary Examiner—George E. Lowrance
Assistant Examiner—Jimmy G. Foster
Attorney, Agent, or Firm—Cole, Jensen & Puntigam

[57] ABSTRACT

A flexible transparent package for transporting and storing an IUD. The package (2) includes a specifically configured seal line such that the IUD (12) may be manipulated into the configured portion (14) of the package and by utilizing the IUD insertion device (10) and the finger and thumb of the operator from the exterior of the package to place the IUD within the insertion device. Whether the IUD is packaged alone or jointly with the insertion device and the necessary plunger (16), the IUD must be shipped and stored in the expanded condition and the present invention permits the compaction and insertion without significantly affecting the sterile conditions of that portion of the device which must be inserted into the body cavity.

2 Claims, 11 Drawing Figures

FIG. 1
FIG. 2
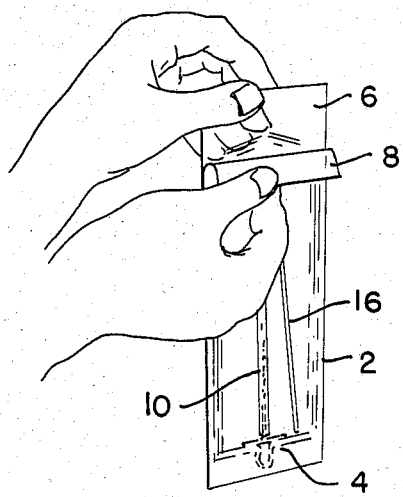
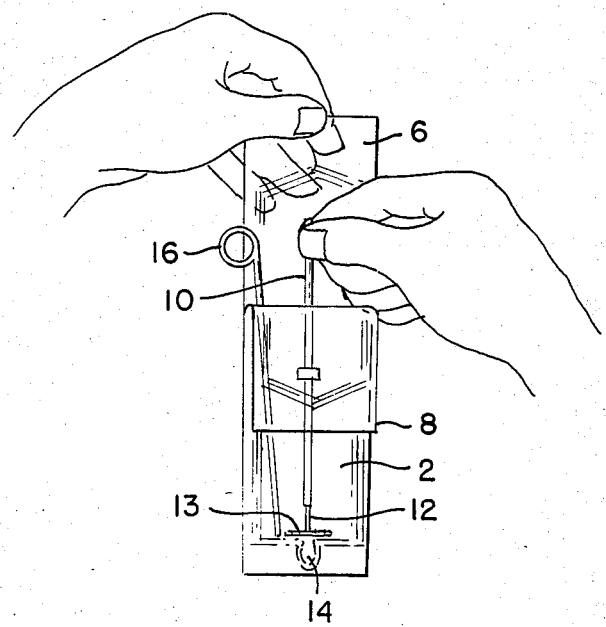
FIG. 3
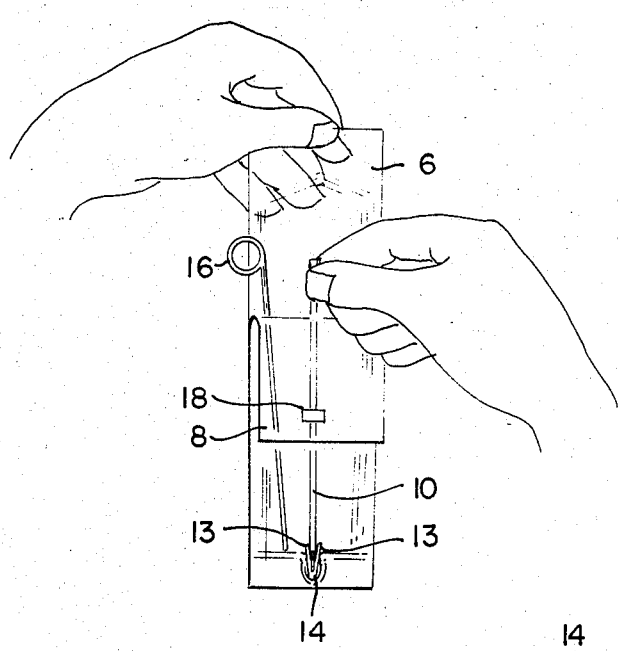
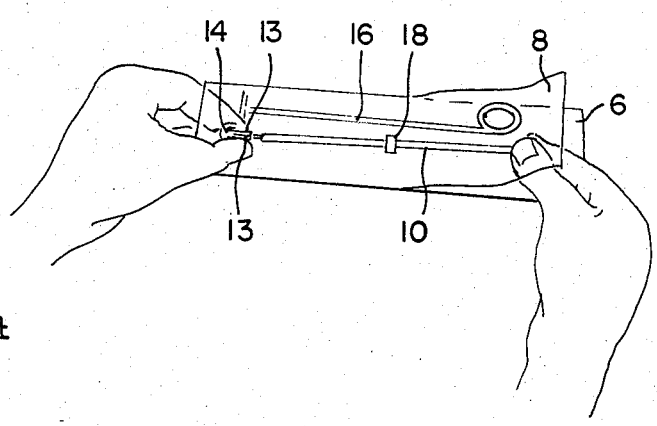
FIG. 4

IUD PACKAGE

This is a continuation of application Ser. No. 509,721, filed June 29, 1983, now abandoned.

TECHNICAL FIELD

The present invention relates to sterile packaging and in particular a package wherein the devices within the package may be manipulated without contaminating them.

BACKGROUND ART

The utilization of an intrauterine contraceptive device for birth control and the method of introducing the device into the human uterus are both well known.

In many countries, and certainly in metropolitan areas of the world, the device is placed under hospital or clinical conditions where the sterility of the IUD itself, the cleanliness of the insertion elements, and the personnel involved are predictable. Under these conditions, the risk of infection is maintained at a minimal level.

It has become apparent and increasingly important that some method of contraception be available to the emerging nations and predominantly rural societies. When dealing with this particular problem, it must be recognized that sterilization and cleanliness are, to a large extent, probabilistic values. Therefore, under field conditions in developing countries effective low cost means for maintaining the sterility of prepackaged sterile IUD's can have a beneficial consequence in reducing the number of infections arising out of routine procedures carried out on a large scale. Further, it has been noted that, the ability and/or willingness of the women to subject themselves to an inconvenience of going to a hospital or clinic in a large city often is limited.

It is important that birth control be made available to those needing or desiring it and be made as convenient as possible for women desiring such devices. It is equally as important that the health and/or lives of the women seeking birth control not be unduly endangered.

It can thus be seen that a device which will be successfully administered in a large variety of conditions must be readily available. This requires that it be packaged in such a way that it can be transported and stored at remote locations. Further, it is important that the device be packaged in a sterile condition and maintained in the sterile condition. Accommodations or devices for sterilizing the IUD itself or the tools required for a safe insertion are often not readily available or, if available, would not necessarily be correctly used. Any breach of the sterile conditions generates a danger of infection.

The utilization of sterile packaging for medical devices of many different kinds is well known in the art and is particularly illustrated by U.S. Pat. No. 3,797,493 granted to Saudek on Mar. 19, 1974. This reference discloses a single use pharmaceutical carrier wherein the seal is broken by forcibly removing a thread or the like which has an enlarged end portion. The removal of the nonwicking thread creates a small opening through which the material may be squeezed. In this device, there is no introduction of foreign material to the interior of the package since the entire process involves moving substance from the interior of the package to the exterior of the package.

U.S. Pat. No. 3,374,788 granted to Rosenthal on Mar. 26, 1968, U.S. Pat. No. 3,398,737 granted to Sheppard et al on Aug. 27, 1968, and U.S. Pat. No. 3,492,990 granted to Clarke on Feb. 3, 1970, each disclose a combination IUD and means for placement (insertion tube) and, further, each disclose a package for the devices which keeps them sterile until ready to use and in a condition for manipulation such that the IUD may be introduced into the inserter and then placed within the uterus with limited amount of contamination.

It is further to be noted that package insert/prospectus put out by manufacturers of IUDs such as Ortho Pharmaceutical of Canada Ltd. fully describe the desired handling and placement of the IUD.

With the exception of the Ortho brochure, the devices described and utilized in the prior art publications specified herein are such that if they are packaged reasonably closely to the insertion tube and the usual string secured to the IUD is passed through the tube, prior to sterilization and/or sealing, then the device could be physically compressed and pulled into the tube by simply pulling the string without requiring the clinician to touch the IUD.

DISCLOSURE OF INVENTION

One of the most popular and successful IUDs is known as the copper T (Cu-T) and although the present invention is particularly described with respect to this device, it is to be understood that the invention applies equally well to other devices which must be compressed for use but because of their particular structure and the safety of the recipient, cannot be compressed in an outwardly or forwardly open condition. Specifically, the proper placement of a device such as the copper T and further, the method of insertion which generates the least hazard for the recipient, requires that the arms of the T be folded back upon the stem and then the contracted device placed within the insertion tube.

Upon proper location within the uterus, the device is removed from the insertion tube and allowed to expand such that the arms extend laterally across the top of and somewhat conforming to the contours of the uterus. Further, when the Cu-T is placed in the insertion tube in this configuration, the leading end of the combination IUD and insertion tube has a relatively smooth surface, thus greatly reducing the chance of perforation of the internal organs.

When the IUD is removed from the tube, the expansion of the arms causes them to lie adjacent to the wall as opposed to laterally thereto, thereby further reducing the possibility of perforation. It is readily apparent that to fold the arms of a copper T or similar device back upon its stem and place it stem first into a tube eliminates the possibility of simply having the retraction string which is attached to the IUD extending through the insertion tube and thus pulling the entire IUD within the tube by simply pulling on the attached string.

With the above noted prior art and problems in mind, it is an object of the present invention to provide a package for an intrauterine device wherein the IUD may be placed within an insertion tube without coming into actual contact with objects exterior to the package.

It is another object of the present invention to provide a package wherein the interior surface of the package is configured such that manipulation of the IUD by the insertion tube will cause it to partially collapse, enabling it to be gripped from the exterior of the package, and collapsed to a point where it may be placed within the insertion tube.

It is another object of the present invention to provide a package, including an IUD, the insertion device, and the plunger for facilitating the final placement, such that these three elements may be assembled and prepared for insertion into the recipient's uterus without the necessity of handling any of the portions which will be placed within the cavity.

BRIEF DESCRIPTION OF THE DRAWINGS

FIG. 1 depicts a sterile, sealed package which contains an IUD, the inserter tube, and the plunger, during the initial stages of opening the package.

FIG. 2 discloses the utilization of the insertion tube to manipulate the IUD to an appropriate position within the package such that the IUD may be partially compressed.

FIG. 3 depicts the manipulation of the IUD from the exterior of the package such that the insertion tube may be placed in position, overlying the stem and collapsed arms of the IUD, holding the arms of a copper T in the collapsed condition.

FIG. 4 depicts the IUD being placed within the insertion tube.

BEST MODE FOR CARRYING OUT THE INVENTION

Figure 5:
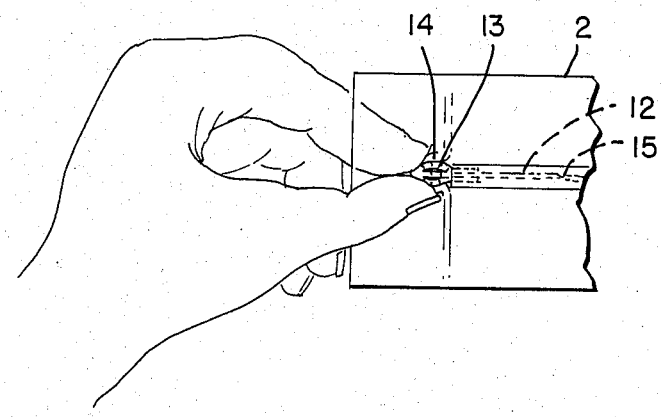
FIG. 5 is an enlarged illustration depicting the manipulation of the IUD from the exterior of the package and with the IUD inserted into proper position within the insertion tube.

As seen in FIG. 1, the package which contains the IUD itself, the insertion tube, and the plunger is opened by tearing from one end. It is to be understood that the end to be opened would be the end which would enclose those portions of the elements of the assemblage necessary to be handled during the insertion and not the portions which will be placed within the recipient's uterus. As seen in this view, the package 2, which has a particularly configured interior seal line 4, described in further detail hereinafter, is separated at the top into two separate portions, back 6 and front 8.

As seen in FIG. 2, the package 2 has been opened approximately half way and by holding the insertion tube 10 at one end, the opposite end has been placed over the stem of a T-type IUD. The insertion tube 10 is then pushed over the stem, forcing the T-type IUD 12 into the configured cavity 14 and, as seen in FIG. 3, causing the arms of the T to fold backwardly toward the stem. It is to be noted that during this entire process the hands have only touched the trailing end of the insertion tube, i.e. that beyond the stop block 18 which controls the depth of penetration of the insertion tube. It is further to be noted that during this entire process, the IUD removal plunger 16 has not been disturbed.

Referring now to FIG. 4, it can be seen that the arms 13 are being folded back adjacent to the stem of the IUD 12 such that the ends of the arms may be placed within the insertion tube in preparation for placement with the uterus. It is to be noted that the compression is being done by hand manipulation from the exterior of the package, thus not violating the sterility of the entire device.

An enlarged view of the final stages of placement of the IUD within the insertion tube is best seen in FIG. 5 where the stem of the IUD 12 is shown in phantom within the insertion tube and the arms 13 are shown in a collapsed condition with the outer tips just within the interior of the insertion tube. Again, it is to be emphasized that this placement within the tube is accomplished without touching the IUD itself.

Figure 6:
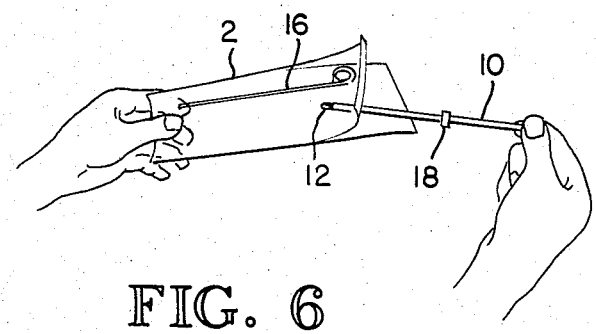
FIG. 6 depicts the removal of the insertion tube and the IUD from the sterile package.

As seen in FIG. 6, the IUD insertion tube, with the IUD in place, is being removed from the package 2 in preparation for insertion.

Figure 7:
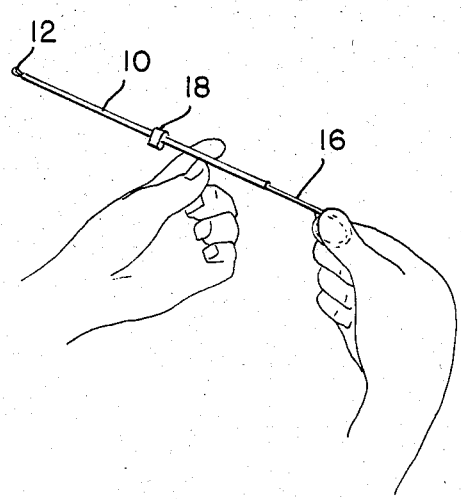
FIG. 7 depicts the placement of the IUD removing plunger within the tube prior to insertion of the device within the human cavity.
Figure 8:
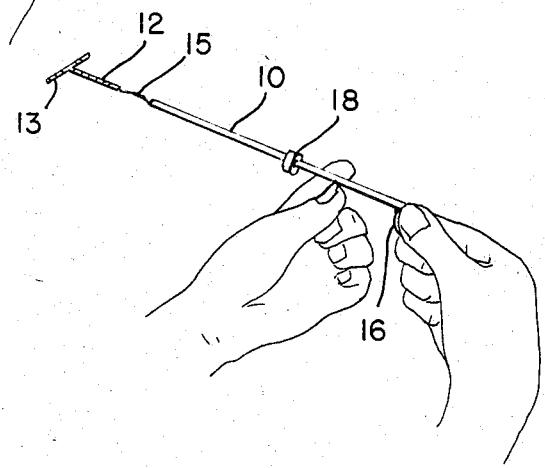
FIG. 8 depicts the removal of the IUD from the insertion tube during placement with the uterus with it expanding to its normal position.

In FIG. 7, the plunger is placed within the insertion tube adjacent to the bottom of the stem of the T and then the entire assembly is ready for insertion. The removable flange or block 18 is adjusted so that it indicates the depth, previously determined by measurement, to which the tube should be placed and the direction in which the arms of the T will open, assuring proper placement. The loaded inserter is introduced through the cervical canal and upwards until the T lies in contact with the fundus. The removable flange should be at the cervix. The T is released by withdrawing the insertion tube approximately ½ inch while the solid rod is maintained in a relatively stable position. The solid rod is withdrawn while holding the insertion tube stationary and then the insertion tube is withdrawn until the strings attached to the IUD are visible. The final condition of the IUD is depicted in FIG. 8.

Figure 9:
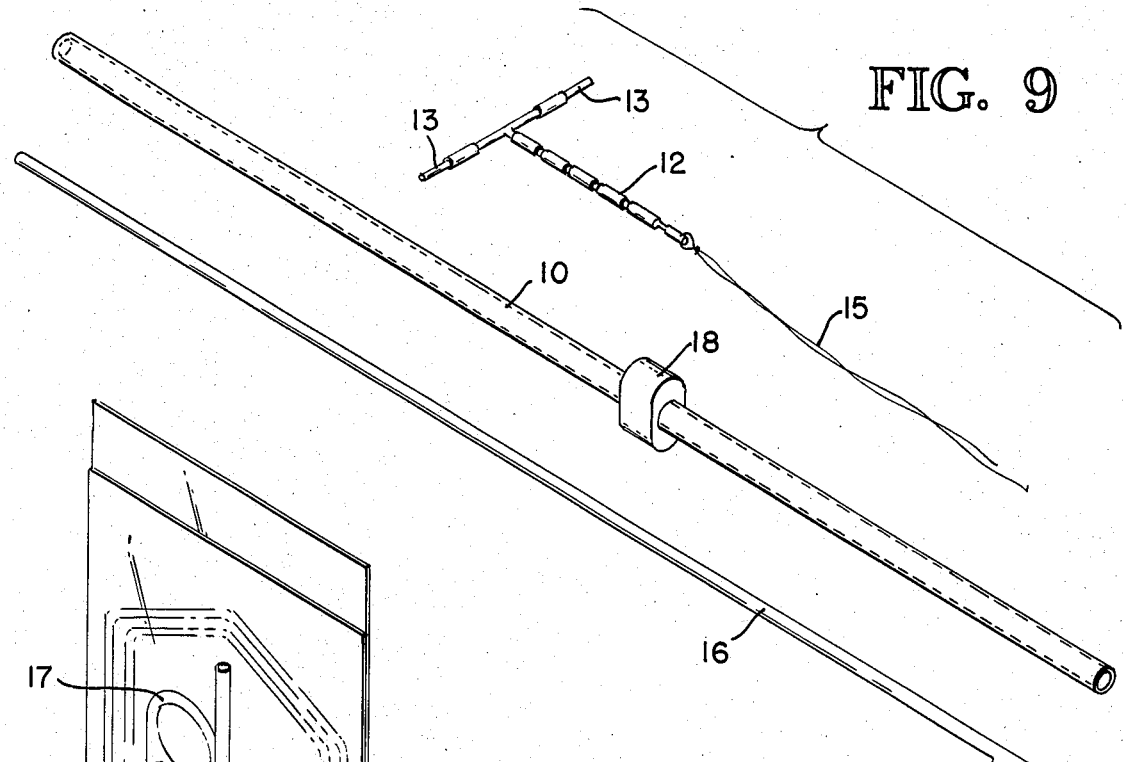
FIG. 9 is an enlarged view of the three devices (the IUD, the insertion tube, and the plunger) which would comprise an entire package.

FIG. 9 depicts the primary elements of the IUD package in approximately real size for clarity and, as can be seen, the IUD 12 has a pair of arms 13 and a string 15. The insertion tube 10 includes a flange 18 which controls the depth of insertion as well as indicating to the person doing the placement, the appropriate time to stop the insertion process as well as displaying the direction of the arms. The plunger 16 is adapted to fit within the tube 10 and includes a handle 17 for ease of handling.

Figure 10:
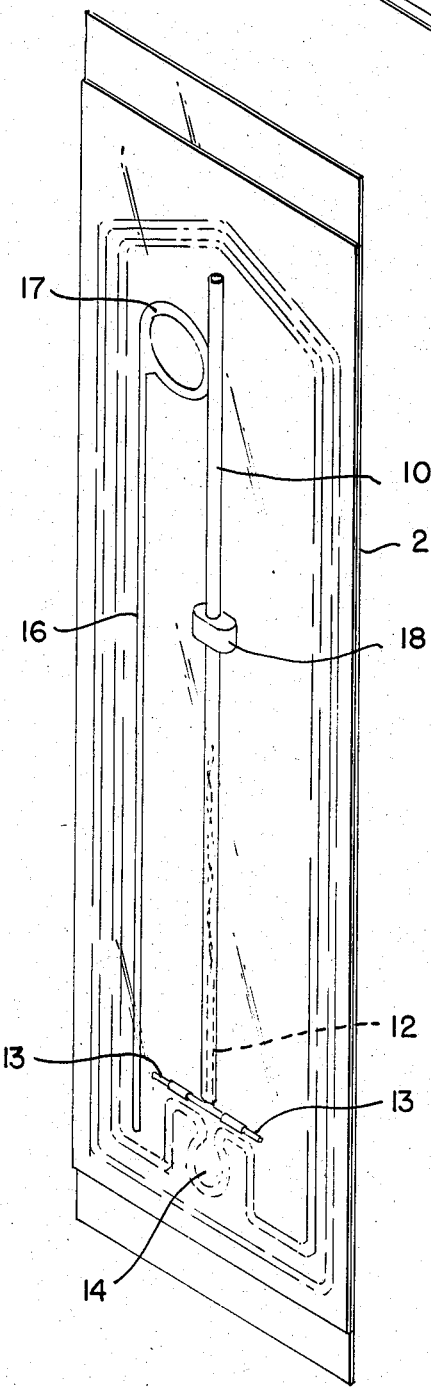
FIG. 10 is a view of the entire package including the three devices in one possible configuration and further disclosing the outline of the configured portion of the package such that the IUD may be manipulated, collapsed and placed within the insertion tube.

For clarity, the entire package is shown in an enlarged condition in one configuration in FIG. 10.

Referring to FIG. 10, the package is fabricated of sealable see-through flexible material which has an exterior general seal 20 which forms a continuous seal about a line approximating the edge of the material. Interior of seal line 20 is a secondary seal line 22 which generally conforms with the outline of seal line 20 but at the end of the package which will contain the T-configured IUD it will include a pair of flat portions 24 extending inwardly towards the center of the package approximately parallel to seal line 20 at that point. A pair of seal lines 26 normal to lines 24 extend towards the center of the package in the other axis and a pair of substantially colinear seal lines 28 normal to seal line 26 extend inwardly towards the longitudinal axis of the package to be interrupted by a circular portion 30 extending outwardly along the axis. It is to be noted that the intersections of flat portions 20 and circular portion 30 form a narrowed neck portion 32.

It is to be noted in this figure that the bottom portion of the package 2 includes a configuration having a valley or void such that when the IUD is pushed downwardly, it will cause the arms of the T to fold back against the stem.

Figure 11:
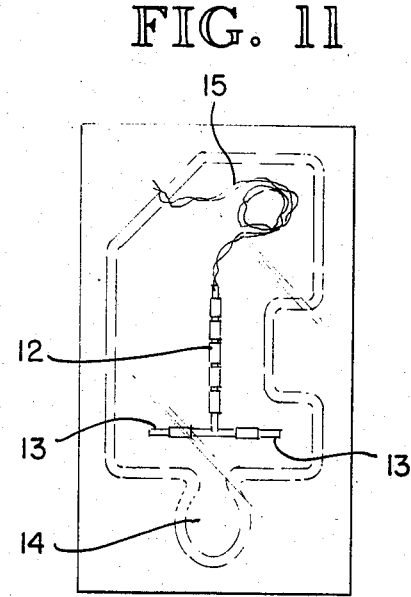
FIG. 11 depicts an IUD package containing an IUD and the configured seam without the insertion tube or removal plunger.

As is noted hereinabove, the IUD could, as an alternative, be shipped separately, in which case the configuration of the package is shown in FIG. 11. It is to be noted that the T is located within the upper portion of the package with string extending downwardly in a loose coil and captured within the corner of the package such that prior to insertion, the inserter will tear off the corner of the package, thus releasing the string without releasing the IUD. The string is then placed within the insertion tube and the insertion tube moved upwardly until it contacts the arms of the T and the T is forced upward into the opening until the arms are partially folded back against the stem. The insertion tube is then partially withdrawn and the entire T, with the arms backward, is placed in the end of the insertion tube.

The sealed portion of FIG. 11 which permits similar manipulation to that described with respect to FIG. 11 includes a seal line 34 which closes the entire package and at one end thereof i.e. that end to be adjacent the arms of the T configured IUD includes a pair of substantially co-linear inwardly directed seal lines 36 interrupted by an outwardly projecting circular portion 38 resulting in a narrowed neck portion 40.

Thus, as can readily be seen, the present invention includes all items necessary for the sanitary placement of an IUD under conditions wherein sanitation is, at best, difficult. The particularly configured package permits the loading of the IUD with a minimal chance of introducing contaminants and, further, that the entire package arrives and is stored in a sanitary condition.

I claim:

1. A sterile package for shipping, storing and manipulating an intrauterine device under sterile conditions comprising:

a flexible sealed envelope of a size to contain an intrauterine device and including as an integral portion thereof, seal lines which totally close the envelope and further, form a section along one side of the package having a substantially flat portion facing the interior of the package interrupted by an outwardly projecting portion in communication with the interior of the package, said projecting portion including a neck adjacent to the flat portion, aid neck being of sufficient dimension to allow the passage of an insertion tube and the arms of the intrauterine device folded along the outside thereof whereby the stem of the IUD may be placed within the tube, the tube and the intrauterine device pushed into the projecting portion, folding the arms back along the tube such that the IUD may be manipulated into the projecting portion, pinched from exterior of the package and placed within the tube ready for placement without removing the IUD from the package or unduly exposing the IUD to contamination.

2. A package as in claim 1, wherein the package is of a size to contain the insertion tube with IUD.

* * * * *